United States Patent [19]

Simpson et al.

[11] 4,052,510
[45] Oct. 4, 1977

[54] 4-ALKYL-2,6-DI(SECONDARY OR TERTIARY ALKYLAMINO) PYRIDINES, COMPOSITIONS THEREOF AND METHODS FOR TREATING DIABETES AND OBESITY

[75] Inventors: William R. Simpson, Mendham; Robert J. Strohschein, Parsippany, both of N.J.

[73] Assignee: Sandoz, Inc., E. Hanover, N.J.

[21] Appl. No.: 673,409

[22] Filed: Apr. 5, 1976

Related U.S. Application Data

[63] Continuation-in-part of Ser. No. 533,941, Dec. 18, 1974, abandoned, which is a continuation-in-part of Ser. No. 460,286, April 12, 1974, abandoned.

[51] Int. Cl.² .................. C07D 213/50; A61K 31/44; A61K 31/455
[52] U.S. Cl. .................. 424/263; 260/296 R; 260/294.9; 260/295.5 R; 260/295.5 A; 260/293.5 B; 260/296 B; 260/566 R; 260/564 R; 260/307 H; 424/266
[58] Field of Search ............ 260/296 R; 424/263

[56] References Cited

U.S. PATENT DOCUMENTS

| 3,946,024 | 3/1976 | Fleckenstein et al. ............ 260/294.9 |
| 3,947,463 | 3/1976 | Fleckenstein et al. ............ 260/294.8 |
| 3,954,782 | 5/1976 | Fleckenstein et al. ......... 260/295.5 A |
| 3,956,294 | 5/1976 | Fleckenstein et al. ............ 260/246 B |

*Primary Examiner*—Henry R. Jiles
*Assistant Examiner*—Robert T. Bond
*Attorney, Agent, or Firm*—Gerald D. Sharkin; Richard E. Vila; Melvyn M. Kassenoff

[57] ABSTRACT

Compounds of the formula

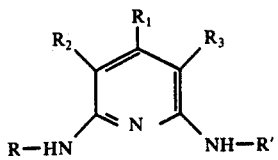

wherein

R is secondary alkyl of 3 to 7 carbon atoms or tertiary alkyl of 4 to 7 carbon atoms,
R' is secondary alkyl of 3 to 7 carbon atoms or tertiary alkyl of 4 to 7 carbon atoms,
$R_1$ is alkyl of 1 to 4 carbon atoms,
$R_2$ is hydrogen, chloro or bromo, and
$R_3$ is hydrogen, —CO—$R_4$ or cyano,
  wherein $R_4$ is alkyl of 1 to 4 carbon atoms, alkoxy of 1 to 3 carbon atoms,

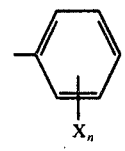

or amino,
  wherein each X is independently alkyl of 1 to 3 carbon atoms, alkoxy of 1 to 3 carbon atoms or halo or two X's on adjacent carbon atoms together are methylenedioxy, with the proviso that the ortho positions of the phenyl ring are free of halo substituents, and
  $n$ is 0, 1, 2 or 3, and the pharmaceutically acceptable acid addition salts thereof,
are useful as anti-obesity and anti-diabetic agents. The compounds wherein $R_2$ is hydrogen and $R_3$ is alkylcarbonyl, benzoyl or substituted benzoyl are synthesized from ketoketenimines and amidines while those wherein $R_2$ is hydrogen and $R_3$ is alkylcarbonyl are also synthesized from isoxazolium salts and ammonia. The compounds wherein $R_2$ is hydrogen and $R_3$ is cyano are synthesized from the corresponding 2,6-dihalopyridines as are many of the other compounds. The compounds wherein $R_2$ is hydrogen and $R_3$ is alkylcarbonyl, alkoxycarbonyl or carbamoyl are synthesized from the corresponding cyano compounds. The compounds wherein $R_2$ is hydrogen and $R_3$ is ($C_{2-4}$alkyl) carbonyl are also synthesized from the corresponding compounds wherein $R_3$ is acetyl. The compounds wherein $R_2$ is chloro or bromo are synthesized from the corresponding compounds wherein $R_2$ is hydrogen and an N-halosuccinimide. The compounds wherein $R_3$ is hydrogen are synthesized from the corresponding alkylcarbonyl compounds or 2,6-dihalopyridines.

30 Claims, No Drawings

4-ALKYL-2,6-DI(SECONDARY OR TERTIARY ALKYLAMINO) PYRIDINES, COMPOSITIONS THEREOF AND METHODS FOR TREATING DIABETES AND OBESITY

This application is a continuation-in-part of application Ser. No. 533,941, filed Dec. 18, 1974, and now abandoned, which is a continuation-in-part of application Ser. No. 460,286, filed Apr. 12, 1974 and now abandoned.

This invention relates to compounds of the formula

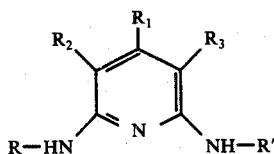

wherein
R is secondary alkyl of 3 to 7 carbon atoms or tertiary alkyl of 4 to 7 carbon atoms,
R' is secondary alkyl of 3 to 7 carbon atoms or tertiary alkyl of 4 to 7 carbon atoms,
$R_1$ is alkyl of 1 to 4 carbon atoms,
$R_2$ is hydrogen, chloro or bromo, and
$R_3$ is hydrogen, —CO—$R_4$ or cyano, wherein $R_4$ is alkyl of 1 to 4 carbon atoms, alkoxy of 1 to 3 carbon atoms,

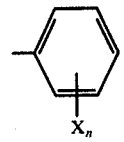

or amino,
wherein each X is independently alkyl of 1 to 3 carbon atoms, alkoxy of 1 to 3 carbon atoms or halo or two X's on adjacent carbon atoms together are methylenedioxy, with the proviso that the ortho positions of the phenyl ring are free of halo substituents, and
n is 0, 1, 2 or 3,
with the proviso that when $R_3$ is cyano, each of R and R' is independently tertiary alkyl of 4 to 7 carbon atoms,
and the pharmaceutically acceptable acid addition salts thereof,
and to processes for their synthesis and intermediates useful in their synthesis. It also relates to the use of the compounds of Formula I, including those wherein $R_3$ is cyano and at least one of R and R' is secondary alkyl of 3 to 7 carbon atoms, and the pharmaceutically acceptable acid addition salts thereof, as anti-obesity and anti-diabetic agents and to pharmaceutical compositions useful in the treatment of obesity and diabetes.

The preferred compounds of Formula I are those wherein R is tertiary alkyl of 4 to 7 carbon atoms, and R' is tertiary alkyl of 4 to 7 carbon atoms,
and the pharmaceutically acceptable acid addition salts thereof, particularly the free bases.

Also preferred are the compounds of Formula I wherein $R_1$ is methyl,
and the pharmaceutically acceptable acid addition salts thereof, particularly the free bases,
as well as the compounds of Formula I wherein $R_3$ is hydrogen or —CO—$R_4'$ (preferably —CO—$R_4$40),
wherein $R_4'$ is alkyl of 1 to 4 carbon atoms,

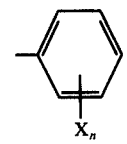

or amino,
wherein X and n are as defined in connection with Formula I,
and the pharmaceutically acceptable acid addition salts thereof, especially the free bases,
and the compounds of Formula I wherein $R_2$ is hydrogen,
and the pharmaceutically acceptable acid addition salts thereof, especially the free bases.

More preferred are the compounds of Formula I wherein
R is a tertiary alkyl of 4 to 7 carbon atoms,
R' is tertiary alkyl of 4 to 7 carbon atoms,
$R_1$ is alkyl of 1 to 4 carbon atoms,
$R_2$ is hydrogen, chloro or bromo, and
$R_3$ is hydrogen or —CO—$R_4''$ (preferably —CO$R_4''$),
wherein $R_4''$ is alkyl of 1 to 4 carbon atoms,

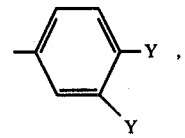

or amino,
wherein X and n are as defined in connection with Formula I, with the proviso that the ortho positions of the phenyl ring are unsubstituted,
and the pharmaceutically acceptable acid addition salts thereof, especially the free bases,
and particularly the compounds of this group wherein
$R_1$ is alkyl of 1 to 3 carbon atoms, and
$R_3$ is hydrogen or —CO—$R_4'''$ (preferably —CO—$R_4'''$),
wherein $R_4'''$ is alkyl of 1 to 3 carbon atoms or

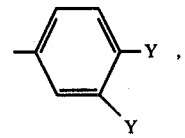

wherein each Y is independently hydrogen, methyl, ethyl, methoxy or ethoxy,
and the pharmaceutically acceptable acid addition salts thereof, especially the free bases,
and more particularly the compounds of this group wherein R is tertiary alkyl of 4 to 6 carbon atoms, and R' is tertiary alkyl of 4 to 6 carbon atoms, with the proviso that R and R' are identical,
and the pharmaceutically acceptable acid addition salts thereof, especially the free bases.

More preferred are the compounds of Formula I wherein

R is tertiary alkyl of 4 to 7 carbon atoms,
R' is tertiary alkyl of 4 to 7 carbon atoms,
$R_1$ is methyl or ethyl,
$R_2$ is hydrogen, chloro or bromo (preferably hydrogen), and
$R_3$ is hydrogen, acetyl or propionyl (preferably acetyl or propionyl),
and the pharmaceutically acceptable acid addition salts thereof, especially the free bases,
and, particularly from the standpoint of ease of synthesis, and compounds of this group
wherein
R and R' are identical, and
$R_1$ is methyl when $R_3$ is acetyl and is ethyl when $R_3$ is propionyl,
and the pharmaceutically acceptable acid addition salts thereof, especially the free bases,
and more particularly the compounds of the foregoing group
wherein
R is t-butyl,
R' is t-butyl, and
$R_2$ is hydrogen,
and the pharmaceutically acceptable acid addition salts thereof, especially the free bases.
Also of interest are the compounds of the formula

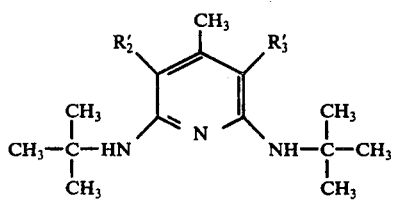

(II), wherein
$R_2'$ is hydrogen or bromo, and
$R_3'$ is hydrogen, acetyl, 4-methoxybenzoyl or cyano,
and the pharmaceutically acceptable acid addition salts thereof, especially the free bases,
and particularly the compounds of this group
wherein $R_3'$ is hydrogen, acetyl or 4-methoxybenzoyl, with the proviso that $R_2'$ must be hydrogen when $R_3'$ is hydrogen or 4-methoxybenzoyl,
and the pharmaceutically acceptable acid addition salts thereof, especially the free bases.
Also preferred are the compounds of the formula

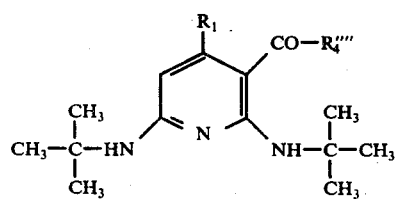

(III), wherein
$R_1$ is alkyl of 1 to 4 carbon atoms, and
$R_4''''$ is alkyl of 1 to 4 carbon atoms,
and the pharmaceutically acceptable acid addition salts thereof, especially the free bases,
and more particularly the compounds of the foregoing group wherein $R_1$ and $R_4''''$ are identical,
and the pharmaceutically acceptable acid addition salts thereof, especially the free bases,
and more particularly the compounds of this group
wherein
$R_1$ is methyl or ethyl, and
$R_4''''$ is methyl or ethyl, with the proviso that $R_1$ and $R_4''''$ are identical,
and the pharmaceutically acceptable acid addition salts thereof, especially the free bases.
Also representative of the compounds of Formula I are those
wherein $R_3$ is carbamoyl ($-CONH_2$),
and the pharmaceutically acceptable acid addition salts thereof, particularly the free bases,
and preferably the compounds of this group wherein $R_2$ is hydrogen,
and the pharmaceutically acceptable acid addition salts thereof, particularly the free bases,
and more preferably the compounds of this group
wherein
R is tertiary alkyl of 4 to 7 carbon atoms,
R' is tertiary alkyl of 4 to 7 carbon atoms, and
$R_2$ is hydrogen,
and the pharmaceutically acceptable acid addition salts thereof, especially the free bases,
and most preferably the compounds of this group
wherein
R is tertiary alkyl of 4 to 6 carbon atoms,
R' is tertiary alkyl of 4 to 6 carbon atoms,
$R_1$ is methyl or ethyl (especially methyl), and
$R_2$ is hydrogen,
and the pharmaceutically acceptable acid addition salts thereof, especially the free bases.
Further representative compounds of Formula I are those
wherein $R_3$ is alkoxycarbonyl the alkoxy moiety of which has 1 to 3 carbon atoms,
and the pharmaceutically acceptable acid addition salts thereof, especially the free bases,
preferably the compounds of this group
wherein $R_2$ is hydrogen,
and the pharmaceutically acceptable acid addition salts thereof, especially the free bases,
more particularly the compounds of this group
wherein
R is tertiary alkyl of 4 to 7 carbon atoms,
R' is tertiary alkyl of 4 to 7 carbon atoms, and
$R_2$ is hydrogen,
and the pharmaceutically acceptable acid addition salts thereof, especially the free bases,
and most preferably the compounds of this group
wherein
R is tertiary alkyl of 4 to 6 carbon atoms,
R' is a tertiary alkyl of 4 to 6 carbon atoms,
$R_1$ is methyl or ethyl (especially methyl),
$R_2$ is hydrogen, and
$R_3$ is methoxycarbonyl or ethoxycarbonyl,
and the pharmaceutically acceptable acid addition salts thereof, especially the free bases.
Further representative compounds of Formula I are those
wherein $R_3$ is hydrogen,
and, especially, the pharmaceutically acceptable acid addition salts thereof,
and particularly the compounds of this group wherein $R_2$ is hydrogen,
and, especially, the pharmaceutically acceptable acid addition salts thereof,
more particularly the compounds of this group
wherein R is tertiary alkyl of 4 to 7 carbon atoms,
R' is tertiary alkyl of 4 to 7 carbon atoms, and
R₂ is hydrogen,
and, especially, the pharmaceutically acceptable acid addition salts thereof,
and particularly the compounds of this group wherein
R is tertiary alkyl of 4 to 6 carbon atoms,
R' is tertiary alkyl of 4 to 6 carbon atoms,
R₁ is methyl or ethyl (especially methyl), and
R₂ is hydrogen,
and, especially, the pharmaceutically acceptable acid addition salts thereof.

The most preferred compound of this application is the compound of the formula

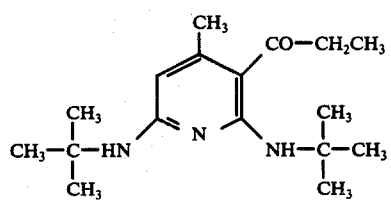

(IV)

and its pharmaceutically acceptable acid addition salts, especially the free base.

Representative of the pharmaceutically acceptable acid addition salts of the compound of Formula IV are the hydrochloride, hydrobromide and methanesulfonate salts; however, the free base is preferred over the salts.

The term "halo" means fluoro, chloro or bromo and, unless otherwise indicated, each alkyl is preferably n-alkyl, more preferably methyl or ethyl and most preferably methyl.

In each of the groups and subgroups, R₂ is preferably hydrogen.

All pharmaceutically acceptable acid addition salts of the compounds of Formula I (i.e., those salts which do not significantly increase the toxicity of the basic compound) are included within the scope of this invention. Included are salts with inorganic acids, e.g., the hydrochloride, hydrobromide, hydroiodide, phosphate (including hydrogen phosphates), metaphosphate, sulfate (including hydrogen sulfate) and perchlorate salts and salts with organic acids, e.g., the acetate, propionate, tartarate, citrate, gluconate, fumarate, malate, maleate, methanesulfonate, ethanesulfonate, benzenesulfonate and p-toluenesulfonate salts. The hydrochloride, hydrobromide and methanesulfonate salts are preferred.

The compounds of Formula I where R₁ is alkyl, R₂ is hydrogen and R₃ is alkylcarbonyl, benzoyl or substituted benzoyl are preferably synthesized by reacting a ketoketenimine of the formula

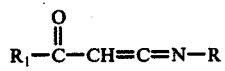

(VI)

with an amidine of the formula

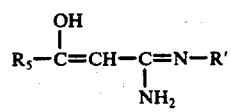

(VII), wherein R₅ is alkyl of 1 to 4 carbon atoms or

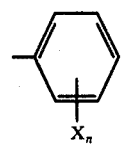

and R, R', R₁, X and n are as defined in connection with
Formula I,
in an inert organic solvent at a temperature of 15° 14 60° C., conveniently 20°–30° C., in the presence of a strong base.

As is well known to those in the art, the reaction time necessary is inversely related to the reaction temperature, i.e., the higher the reaction temperature, the shorter the reaction time. It is, therefore, impossible to give a precise reaction time. However, a reaction time of 30-180 minutes is generally acceptable with a reaction time of 30-120 minutes being preferred.

The reaction solvent is not critical. Any inert organic solvent that does not have an acidic hydrogen atom (proton) in which the reactants are soluble, or at least partially soluble, and whose boiling point is at or above the desired reaction temperature and whose freezing point is below the desired reaction temperature may be used. An inert solvent is one that under the reaction conditions employed, does not react with any of the reactants or the desired product and that does not otherwise interfere with the reaction by, for example, reacting with any transitory or long-lived intermediate involved. Among the inert solvents that are suitable are symmetrical and unsymmetrical dialkyl ethers having a total of at least 5 carbon atoms and preferably no more than 10 carbon atoms, cyclic ethers (e.g., p-dioxane and tetrahydrofuran), liquid symmetrical and unsymmetrical 2-lower alkoxyethyl ethers (e.g., bis-2-methoxyethyl ether and bis-2-ethoxyethyl ether) and symmetrical and unsymmetrical dilower alkyl ethers of ethylene glycol (e.g., 1,2-dimethoxyethane, 1,2-diethoxyethane and 1-ethoxy-2-methoxyethane), and mixtures of these solvents. Tetrahydrofuran and p-dioxane, and mixtures thereof, are particularly suitable. Mixtures of the foregoing solvents with liquid alkanes, e.g., alkanes having 6 to 10 carbon atoms, are also particularly well suited.

The molar ratio of the amidine of Formula VII to the ketoketenimine of Formula VI is usually 1:1; however, a small molar excess (e.g., up to 10%) of the ketoketenimine is occasionally employed.

Any strong base can be employed, for example lithium lower alkyls (e.g., methyl lithium and n-butyl lithium), phenyl lithium, sodium or potassium lower alkoxides (e.g, sodium methoxide and potassium t-butoxide), alkali metal hydroxides (e.g., lithium, sodium and potassium hydroxide), metal hydrides (e.g., sodium hydride and calcium hydride) and lithium di-isopropyl amide. However, non-nucleophilic bases are preferred. The base must be stronger than the amidine employed. Lithium di-isopropyl amide and n-butyl lithium are particularly convenient bases. Generally, one equivalent of base (relative to the amidine) is employed.

The reaction is generally run under an inert atmosphere (e.g., nitrogen, helium, neon, argon, krypton or xenon) by adding a solution of the strong base to the amidine and then adding a solution of the ketoketenimine to the resulting solution after the initial exothermic reaction has ceased.

The foregoing synthesis often results in the formation of varying amounts of a compound whose structure has not as yet been determined and which will hereafter be referred to as a compound of Formula VIII or Compound VIII. The compounds of Formula VIII are postulated to be intermediates in the synthesis of the compounds of Formula I. The precise factors that govern the relative amounts of the compounds of Formula I and the compounds of Formula VIII isolated are not as yet well defined. (Compound VIII was a minor product of Example 4(a) (the 0.5 g. of white solid that was insoluble in chloroform/water) and the major product of Example 6.)

However, the formation of compounds of Formula VIII is not detrimental to the synthesis of compounds of Formula I. Any compound of Formula VIII formed can be converted to a compound of Formula I by heating at a temperature of 35°-70° C., preferably 40°-60° C., for 1-60 minutes, preferably 5-30 minutes, in an inert organic solvent in which it is soluble, or in a mixture of inert organic solvents or a mixture of water and one or more organic solvents miscible with water in which it is soluble. Lower alkanols such as methanol, ethanol and iso-propanol and mixtures thereof with water are particularly convenient solvents for the conversion. Among the other organic solvents that are useful are those that were indicated to be useful for the reaction of the amidine of Formula VII and the ketoketenimine of Formula VI.

Compounds of Formula I wherein the R and R' groups differ and/or the $R_1$ and $R_4$ groups differ can be synthesized using an amidine of Formula VIi whose R' and/or $R_5$ groups differ from the R and/or $R_1'$ groups of the ketoketenimine of Formula VI. The resulting mixture, if one is obtained, can be separated by conventional techniques, e.g., fractional crystallization and/or gradient elution column chromatography using an adsorbent such as silica and eluents such as mixtures of methanol and chloroform.

The foregoing process is particularly preferred for compounds of Formula I wherein R is tertiary alkyl of 4 to 7 carbon atoms, even more preferred for compounds wherein R and R' are both tertiary alkyl of 4 to 7 carbon atoms, $R_1$ is alkyl of 1 to 3 carbon atoms and $R_4$ is alkyl of 1 to 3 carbon atoms, phenyl or substituted phenyl, and still more preferred for compounds wherein R and R' are t-butyl and $R_1$ and $R_4$ are methyl, ethyl or n-propyl (particularly methyl or ethyl).

The amidines of Formula VII are synthesized by reacting a ketoketenimine of the formula

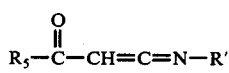

(IX), wherein
R' and $R_5$ are as defined in connection with Formula VII,
with ammonia or by reacting an isoxazolium salt of the formula

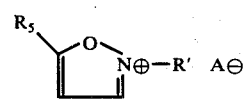

(X), wherein
R' and $R_5$ are as defined in connection with Formula VII, and
A⁻ is a non-interfering anion, e.g., perchlorate, tetrafluoroborate, methylsulfate, ethylsulfate, bisulfate chloride, bromide, iodide or p-toluenesulfonate,
with ammonia. Either reaction is suitably effected by adding a solution of the compound of Formula IX or X in an inert organic solvent, e.g., methylene chloride, to a solution of anhydrous liquid ammonia in an inert organic solvent, preferably the same solvent, i.e., methylene chloride, with stirring at −40°- −60° C. for 5-60 minutes. Although not essential, an inert atmosphere (as defined above) is usually employed. A large molar excess of liquid ammonia to isoxazolium salt or ketoketenimine (e.g., 10-1000 mols) is generally employed.

The preferred amidines of Formula VII are those of the formula

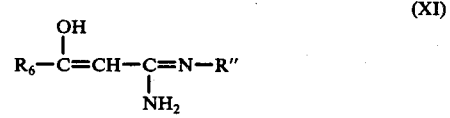
(XI)

wherein
R" is tertiary alkyl of 4 to 7 carbon atoms, and $R_6$ is alkyl of 1 to 3 carbon atoms or

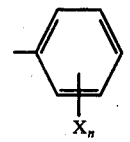

wherein X and n are as defined in connection with Formula I,
and particularly the compounds of this group
wherein $R_6$ is methyl, ethyl or

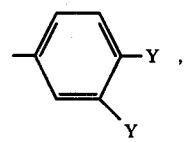

wherein each Y is as defined above, and more particularly the compounds of the foregoing group
wherein R" is t-butyl.

Also preferred are the amidines of Formula XI wherein R" is t-butyl,
and particularly those of this group
wherein $R_6$ is alkyl of 1 to 3 carbon atoms, preferably methyl, ethyl or n-propyl.

The ketoketenimines of Formulae VI and IX are known or can be produced by conventional means from isoxazolium salts of the formula

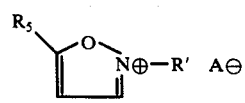
(X), wherein
R' is secondary alkyl of 3 to 7 carbon atoms or tertiary alkyl of 4 to 7 carbon atoms, and $R_5$ is alkyl of 1 to 4 carbon atoms or

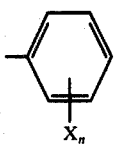

wherein X and $n$ are as defined in connection with Formula I and $A^-$ is as defined above.

See Woodward et al., J. Amer. Chem. Soc. 88, 3169-3170 (1966), which is hereby incorporated by reference. The ketoketenimines are usually stored at or below 0° C. to inhibit decomposition.

The compounds of Formula I wherein $R_1$ is alkyl, $R_2$ is hydrogen and $R_3$ is alkylcarbonyl, benzoyl or substituted benzoyl may also be synthesized by reacting an isoxazolium salt of Formula X with ammonia at a temperature of 15°-30° C., preferably 15;20 -25° C. An inert atmosphere (e.g., nitrogen, helium, neon, argon, krypton or xenon, or a mixture thereof, preferably nitrogen) is generally employed.

As is well known to those in the art, the reaction time necessary is inversely related to the reaction temperature, i.e., the higher the reaction temperature, the shorter the reaction time. It is, therefore, impossible to give a precise reaction time. However, a reaction time of 2-10 days is generally acceptable with a reaction time of 3-5 days being particularly convenient.

While the molar ratio of ammonia to isoxazolium salt can be as low as 3:2, a large excess of ammonia is generally employed, e.g., 5-200 mols ammonia per mol of isoxazolium salt.

Any inert organic solvent in which the reactant is at least partially soluble whose freezing point is below the desired reaction temperature and boiling point is above the desired reaction temperature may be employed. An inert solvent is one that does not interfere with the desired reaction by reacting with the starting material (the isoxazolium salt), the desired product (the compound of Formula I) or any intermediates (long-lived or transitory, e.g., a ketoketenimine of Formula VI and/or an amidine of Formula VII) involved. Among the inert solvents that are suitable are halogenated lower alkanes (e.g., methylene chloride, chloroform, 1,2-dichloroethane, 1,2-dibromoethane, 1,1,1-trichloroethane and 1-bromo-2-chloroethane), symmetrical and unsymmetrical dialkyl ethers having a total of at least 5 carbon atoms and preferably no more than 10 carbon atoms, cyclic ethers (e.g., p-dioxane and tetrahydrofuran), N,N-dimethylacetamide and formic acid amides (e.g., formamide and its N-monolower alkyl and N,N-dilower alkyl derivatives such as N-ethylformamide, N,N-dimethylformamide, N,N-diethylformamide and N-methyl-N-ethylformamide) and mixtures of these solvents. The halogenated lower alkanes are preferred with methylene chloride being particularly preferred.

A mixture of two isoxazolium salts wherein the R' groups and/or the $R_5$ groups are different can be employed to give compounds of Formula I wherein R and R' and/or $R_1$ and $R_4$ differ. The resulting mixtures can be separated by conventional techniques such as fractional crystallization and column chromatography using an adsorbent such as silica and eluents such as mixtures of methanol and chloroform.

The isoxazolium salts of Formula X are known or can be produced by a conventional quaternization of the corresponding isoxazoles with a strong alkylating agent, e.g., a dialkyl sulfate or a mixture of a tertiary alkanol, e.g., t-butanol, and perchloric acid. See, for example, Woodward et al., J. Amer. Chem. Soc. 83, 1007-1009 (1961), Woodward et al., J. Amer. Chem. Soc. 83, 1010-1012 (1961), Woodward et al., J. Amer. Chem. Soc. 88, 3169-3170 (1966) and Woodward et al., J. Org. Chem. 31, 2039-2040 (1966). The isoxazoles are either known or can be prepared by conventional processes from known precursors.

The compounds of Formula I wherein $R_2$ is hydrogen and $R_3$ is hydrogen, cyano, benzoyl, substituted benzoyl or carbamoyl, including those wherein at least one of R and R' is secondary alkyl and $R_3$ is cyano, are synthesized from the corresponding 2,6-dihalopyridines and at least two equivalents of an amine (or one equivalent of each of two different amines) as disclosed in Netherlands Application 7,308,294 (to which German Offenlegungsschrift 2,230,392, Belgian Pat. No. 801,342 and British Pat. No. 1,420,987 are equivalent), U.S. Pat Nos. 3,853,895 and 3,899,478, Belgian Pat. No. 776,859 (to which British Pat. Nos. 1,377,505 and 1,377,506 are equivalent) and German Offenlegungsschriften 2,211,663 and 2,216,570. In addition to these compounds, some of the other compounds of Formula I can also be synthesized by this process. See also Bernstein et al., J. Amer. Chem. Soc. 69, 1151-1158 (1947).

The required 2,6-dihalopyridines can be synthesized from the corresponding 2,6-dihydroxypyridines as set forth in the aforementioned Netherlands appliction and its German, Belgian and British equivalents. The 2,6-dihydroxypyridines are known or can be synthesized by conventional processes from known precursors. See, for example, U.S. Pat. Nos. 3,487,066 and 3,619,112.

The compounds of Formula I wherein $R_2$ is hydrogen and $R_3$ is alkylcarbonyl, benzoyl or benzoyl substituted by up to 3 alkyl groups may be obtained from the corresponding compounds wherein $R_3$ is cyano by treatment with at least three equivalents, conveniently 3.01-20 equivalents, of an alkyl, preferably n-alkyl, phenyl or phenyl substituted by up to 3 alkyl groups lithium, in an inert organic solvent, e.g., ether or tetrahydrofuran, a mixture thereof, at reflux temperature for 2-24 hours to obtain the corresponding imine which is hydrolyzed to the corresponding ketone by heating in very dilute acid, e.g., 0.01-0.1 N. acetic acid for a short period of time, e.g., 5-120 minutes, at a temperature of 60°-100° C.

The compounds of Formula I wherein $R_2$ is hydrogen and $R_3$ is alkylcarbonyl, benzoyl or substituted benzoyl (excluding substituted benzoyl groups having one or more halo substituents) may also be obtained by another two-step reaction sequence from the corresponding compounds wherein $R_3$ is cyano. The starting material is first treated with at least three equivalents, conveniently 3.01-20 equivalents, of an alkyl, preferably n-alkyl, phenyl or substitited phenyl (excluding halo substituted) magnesium chloride, bromide or iodide, preferably bromide or iodide, i.e., an appropriate Grignard reagent, under conventional Grignard reaction conditions, i.e., in an inert organic solvent such as ether or tetrahydrofuran, or a mixture thereof, at 0°-100° C., preferably reflux temperature, for 2-24 hrs., to obtain the corresponding imine. The imine is then hydrolyzed to the corresponding ketone by heating in very dilute acid, e.g., 0.01-0.1 N. acetic acid for a short period of time, e.g., 5-120 minutes, at a temperature of 60°-100° C.

The compounds of Formula I wherein $R_2$ is hydrogen and $R_3$ is alkoxycarbonyl are synthesized from the corresponding compounds wherein $R_3$ is cyano by refluxing for ½-3 hours in an alkanol of 1 to 3 carbon atoms saturated with gaseous hydrogen chloride followed by hydrolysis with water.

The compounds of Formula I wherein $R_2$ is hydrogen and $R_3$ is propionyl, n-butyryl, n-pentanoyl or 3-methylbutyryl can also be synthesized from the corresponding compounds wherein $R_3$ is acetyl and a secondary or, preferably, primary $C_{1-3}$alkyl bromide or, preferably, iodide in the presence of a strong base at a temperature of $-30°-40°$ C., conveniently $0°-10°$ C., for 5-60 minutes, conveniently 10-30 minutes, under an inert atmosphere (as defined above).

The strong bases and reaction solvents which may be employed in the reaction of a ketoketenimine of Formula VI and an amidine of Formula VII are also suitable for this reaction. Preferably, however, the base is other than an alkali metal alkoxide or hydroxide and most preferably is a lithium lower alkyl with n-butyl lithium being particularly convenient. It goes without saying that the selected reaction solvent must be a liquid at the reaction temperature employed.

Generally, one equivalent of the strong base per equivalent of the compound of Formula I wherein $R_2$ is hydrogen and $R_3$ is acetyl is employed; however, a small excess (up to 5%) may by used. Only one equivalent of the primary or secondary $C_{1-3}$alkyl bromide or iodide per equivalent of the compound of Formula I wherein $R_2$ is hydrogen and $R_3$ is acetyl need be employed. However, 1.05-2 equivalents are conveniently employed.

This reaction is generally run by slowly adding a solution of the strong base to a solution of the compound of Formula I wherein $R_3$ is acetyl, stirred under nitrogen, at a rate slow enough to prevent the temperature of the reaction mixture from rising above the desired temperature, e.g., 0-20° C., and, after the initial exothermic reaction has ceased, adding the primary or secondary $C_{1-3}$alkyl bromide or iodide. If necessary, the obtained product can be purified by column chromatography using a silica gel column and an eluent such as 50% toluene/hexane or a mixture of methanol and chloroform.

The compounds of Formula I wherein $R_2$ is hydrogen and $R_3$ is carbamoyl are synthesized from the corresponding compounds wherein $R_3$ is cyano by treatment with a large molar excess of hydrogen peroxide and a catalytic amount of a base such as sodium hydroxide in a solvent such as a lower alkanol, e.g., methanol, at 20°-50° C. for 2-4 hours. The reaction is usually effected by adding the hydrogen peroxide to a solution of the starting material followed by addition of a solution of the base. Since the reaction is initially exothermic, the reaction mixture must be cooled when the temperature reaches the maximum desired reaction temperature. At the conclusion of the exothermic stage, the reaction mixture is usually heated to maintain the desired reaction temperature.

The compounds of Formula I wherein $R_1$ is alkyl and $R_2$ is chloro or bromo are synthesized from the corresponding compounds wherein $R_2$ is hydrogen by treatment with about one equivalent (e.g., 1-1.02 equivalents) of N-chlorosuccinimide or N-bromosuccinimide in an inert organic solvent, e.g., carbon tetrachloride or a lower alkanol such as ethanol, or a mixture thereof, at a temperature of 0°-30° C., conveniently 20°-25° C., for ½-12 hours, preferably 1-3 hours. the halogenation can also be effected using 1 mol. of a solution of gaseous chlorine or liquid bromine in an inert organic solvent at 0°-25° C., preferably 0°-10° C., for ½-12 hours, preferably 1-3 hours. See, in this connection, U.S. Pat. No. 3,776,918.

The compounds of Formula I wherein $R_3$ is hydrogen can also be synthesized from the corresponding compounds wherein $R_3$ is alkylcarbonyl by acid hydrolysis. Suitably, slightly more than one equivalent of aqueous acid, e.g., 1.02-1.1 equivalents, are employed. The amount of water present conveniently is 1.2-2 equivalents. The solvent is conveniently a lower alkanol such as methanol. A reaction temperature of 50°-70° C. (limited by the boiling point of the solvent) and a reaction time of 1 ½-5 hours, preferably 2 ½-4 hours, are wellsuited. The alkylcarbonyl groups can also be hydrolyzed by treatment with about one equivalent (e.g., 1.01-1.5 equivalents) of hydroxylamine hydrochloride in a lower alkanol, e.g., methanol, for 5-120 minutes, at 20°-50° C., preferably 20°-30° C.

The compounds of Formula I in free base form can be converted into their pharmaceutically acceptable acid addition salts by conventional means. However, with those compounds of Formula I that are particularly sterically hindered, a large excess of acid may be needed to drive the reaction to completion. Likewise, any acid addition salt can be converted into the free base by conventional means, e.g., by partition between aqueous 2N. sodium hydroxide and chloroform. Hence, any acid addition salt that is not suitable for pharmaceutical use may be converted by conventional means into a free base or pharmaceutically acceptable acid addition salt that is suitable for such use.

The compounds of Formula I and their pharmaceutically acceptable acid addition salts are useful as anti-obesity and anti-diabetic agents as indicated by (a) glucose transport tests carried out in male Wistar rats and (b) antihyperglycemic tests carried out in male ICR mice. The compounds of Formula I wherein $R_3$ is hydrogen are particularly suitable as anti-diabetic agents while the remaining compounds are particularly suitable as anti-obesity agents. a. Glucose transport test: Male Wistar rats are dosed orally with 0.5-80 mg./kg. body weight of the test compound after at least 20 hours of fasting. One hour after receiving the drug, each animal is sacrificed and the upper small intestine is removed and washed with glucose-saline. A 5 cm. section of the intestine is everted so that the mucosal surface is on the outside. One end of the segment is tied and the center of the sac so formed is filled with oxygen saturated Kreb's bicarbonate buffer. The other end is then closed to form a sac which is then incubated in 10 ml. of oxygen saturated bicarbonate buffer for 60 minutes at 37° C. Both the outside and inside solutions contain initially 0.3% of glucose. At the end of the incubation time, the glucose content of the outer (mucosal) and the inner (serosal) solution is determined using the standard Auto Analyzer procedure. Similar tests are run similtaneously with control animals receiving only the vehicle. The percent inhibition of glucose transport causd by the drug is calculated from the formula $$I = 100 - \left( \frac{S_t - M_t}{S_c - M_c} \times 100 \right),$$

wherein

I = percent inhibition, $S_t$ = glucose concentration (mg.%) of serosal fluid at the end of an experiment in the drug-treated animal, $S_c$ = glucose concentration (mg.%) of serosal fluid at the end of an experiment in the control animal, $M_t$ = glucose concentration (mg.%) of mucosal fluid at the end of an experiment in the drug-treated animal, and $M_c$ = glucose concentration (mg.%) of mucosal fluid at the end of an experiment in the control animal.

b. Anti-hyperglycemic test: 6–8 week old adult male ICR mice having a body weight of 30–35 g. are dosed orally with 75–200 mg./kg. body weight of the test compound after 16 hours of fasting. A control group receiving 0.5% carboxymethyl cellulose vehicle is run concurrently. One and one-half hours after the mice are dosed with the test compound or the carboxymethyl cellulose vehicle, a glucose challenge of 2 g./kg. body weight p.o. is administered. (See Laboratory Animal Digest 7 (4), 76 (1972).). Twenty-five minutes later the mice are anesthetized with sodium hexobarbital (85 mg./kg. body weight i.p.). Exactly 30 minutes following administration of the glucose challenge, the blood is collected via cardiac puncture. The blood is placed in an Auto Analyzer cup containing 0.025 cc of a heparin preparation containing 1000 units/ml. and the samples are capped, shaken and kept in an ice bucket. The glucose content of each sample is measured by the standard Auto Analyzer potassium ferric cyanide method (#N-2b). To validate the test a known anti-hyperglycemic standard is included each time the test is run. The activity of the compound is calculated from the formula $$A = \frac{G_c - G_t}{G_c} \times 100,$$

wherein

A = % reduction of the glucose concentration of the blood achieved by the test compound, $G_c$ = glucose concentration (mg.%) of the blood of the control animals, and $G_t$ = glucose concentration (mg.%) of the blood of the animal receiving the test compound.

The precise dosage of the compound of Formula I, or a pharmaceutically acceptable acid addition salt thereof, to be employed depends upon several factors including the severity of the condition being treated, the mode of administration and the particular compound employed. However, in general, satisfactory results in the treatment of either obesity or diabetes are obtained when a compound of Formula I, or a pharmaceutically acceptable acid addition salt thereof, is adminstered at a daily dosage of 1–200 mg./kg. body weight p.o. or a dosage of about 75–1500 mg. for most larger mammals. In general, oral adminstration requires a higher dose than does intravenous adminstration. Usually, a small dosage is adminstered initially and the dosage is gradually increased until the optimal dosage for the host under treatment is determined. The daily dosage is usually divided into two to four equal portions. A typical dosage for larger mammals is 50–150 mg. three times a day.

The compounds of Formula I and their pharmaceutically acceptable acid addition salts may be formulated into conventional pharmaceutical compositions and adminstered by conventional modes of admistration for the treatment of obesity and diabetes. The compounds of each subgroup set forth in the specification and/or claims may be formulated into conventional pharmaceutical compositions. As set forth above, the compounds wherein $R_3$ is hydrogen are particularly suitable for the treatment of diabetes while the remaining compounds of Formula I (and every subgroup) are particularly suitable for the treatment of obesity.

The compounds may be combined with pharmaceutically acceptable carriers and other conventional pharmaceutical adjuvants and administered orally in the form of tablets, dispersible powders, granules, capsules, elixirs, suspensions and the like or parenterally in the form of an injectable solution or suspension. The composition may be prepared by conventional means and may contain one or more conventional adjuvants such as sweetening agents (oral compositions only), other flavoring agents (oral compositions only), coloring agents (oral compositions only) and preserving agents.

Tablets may contain the active ingredient in admixture with conventional excipients, i.e., inert diluents such as calcium carbonate, sodium carbonate, lactose, talc and sodium citrate, granulating and disintegrating agents, e.g., starch, gum tragacanth and alginic acid and also certain complex silicates, binding agents, e.g., starch, gelatin and acacia, and lubricating agents, e.g., magnesium stearate, stearic acid, talc and sodium lauryl sulfate. The tablets may be uncoated or coated by known techniques to delay disintegration and absorption in the gastrointestinal tract and thereby provide a sustained action over a longer period.

Capsules may contain a compound of Formula I, or a pharmacueutically acceptable acid addition salt thereof, alone or admixed with an inert solid diluent, e.g., calcium carbonate, calcium phosphate, kaolin, lactose and high molecular weight polyethylene glycols.

Suspensions, syrups and elixirs may contain a compound of Formula I, or a pharmaceutically acceptable acid addition salt thereof, in admixture with any of the conventional excipients utilized for the prepartion of such compositions i.e., suspending agents, e.g., methylcellulose, tragacanth and sodium alginate, wetting agents, e.g., lecithin, polyoxyethylene stearate and polyoxyethylene sorbitan monooleate, preservatives, e.g., ethyl p-hydroxybenzoate, and diluents, e.g., ethanol, propylene glycol and glycerin.

Injectable compositions may contain salt and should, if necessary, be buffered to render them isotonic and are sterile.

The preferred pharmaceutical compositions from the stand-point of ease of preparation and administration are solid composition, particularly tablets and hard-filled capsules.

A typical dosage unit may contain 25 to 1000 mg. of a compound of Formula I, or a pharmaceutically acceptable acid addition salt thereof, more typically 75 to 1000 mg.

A representative formulation prepared by conventional techniques for encapsulation in a hard gelatin capsule is:

| A. | Compound of Formula I, e.g., | |
|---|---|---|
| | the compound of Example 4 | 200 mg. |
| | Lactose (spray-dried) | 160 mg. |
| | Colloidal silica (Cab-O-Sil) | 6 mg. |
| | Alginic acid | 60 mg. |
| B. | Compound of Formula I, e.g., | |
| | the compound of Example 16 | 100 mg. |
| | Powdered lactose | 100 mg. |

Preferably, the active ingredient is micronized by conventional means and then mixed with the diluent.

-continued

| C. | Compound of Formula I, e.g., | |
|---|---|---|
| | the compound of Example 16 | 50 mg. |
| | Powdered lactose | 50 mg. |
| | Preferably, the active ingredient is micronized by conventional means and then mixed with the diluent. | |
| D. | Compound of Formula I, e.g., | |
| | the compound of Example 15 | 200 mg. |
| | Powdered lactose | 200 mg. |
| | Preferably, the active ingredient is micronized by conventional means and then mixed with the diluent. | |
| E. | Compound of Formula I, e.g., | |
| | the compound of Example 16 | 25 mg. |
| | Powdered lactose | 25 mg. |
| | Preferably, the active ingredient is micronized by conventional means and then mixed with the diluent. | |

A typical tablet may contain:

| A. | Compound of Formula I, e.g., | | |
|---|---|---|---|
| | the compound of Example 4 | 100 | mg. |
| | Gum tragacanth | 10 | mg. |
| | Lactose (spray-dried) | 197.5 | mg. |
| | Corn starch | 25 | mg. |
| | Talc | 15 | mg. |
| | Magnesium stearate | 2.5 | mg. |
| B. | Compound of Formula I, e.g., | | |
| | the compound of Example 16 | 150 | mg. |
| | Gum tragacanth | 10 | mg. |
| | Lactose (spray-dried) | 222.5 | mg. |
| | Corn starch | 25 | mg. |
| | Talc | 15 | mg. |
| | Magnesium stearate | 2.5 | mg. |

As is evident from the foregoing, many of the compounds of this application are also useful as intermediates in the synthesis of other compounds of this application. In addition, the compounds of Formula I wherein $R_3$ is cyano, particularly those wherein $R_1$ is methyl or ethyl, especially methyl, (including those wherein R and R' are secondary alkyl of 3 to 7 carbon atoms but particularly those wherein R and R' are tertiary alkyl of 4 to 7 carbon atoms) are useful for the synthesis of various 3-formylpyridines, as disclosed in our copending application Ser. No. 655,428, which are also useful for the treatment of obesity and diabetes.

As is evident to those in the art, the compounds of Formula I may exist in three principal tautomeric forms, I(a), I(b) and I(c).

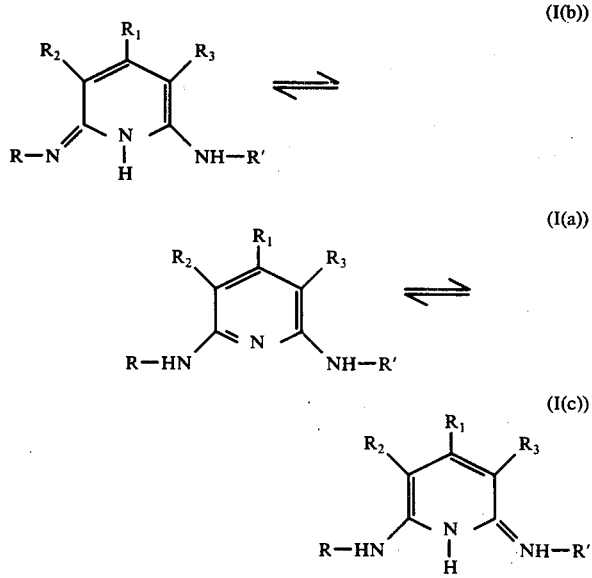

which rapidly interconvert. For simplicity, Formula I(a) has been used exclusively throughout the specification and claims since it is believed to be the most stable and predominant form. However, it should be understood that Formula I is nothing more than a shorthand notation for Formulae I(a)–I(c) and any other possible tautomeric form. It goes without saying that all other formulae directed to the compounds of Formula I (e.g., Formulae II–V, XV–XVII and XIX–XXII) also embrace their resepctive tautomeric forms, i.e., the corresponding formulae wherein the hydrogen atoms (protons) and double bonds are as in Formulae I(b) and I(c) and any other possible form.

As is also evident to those in the art, the amidines of Formula VII may also exist in tautomeric forms, VII(a)–VII(d),

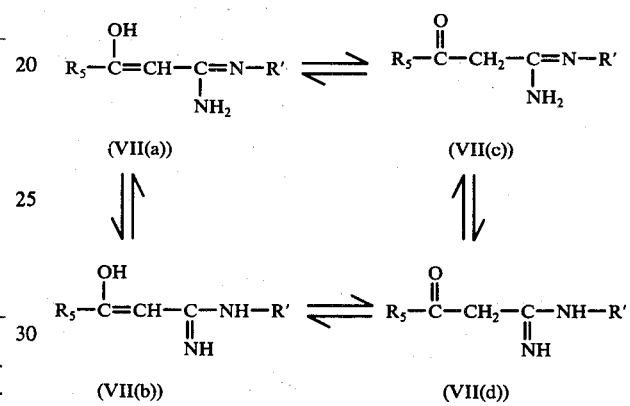

wherein the carbon-carbon double bonds are cis or trans, i.e., the —OH and —H groups are cis or trans to each other, and hydrogen bonded forms thereof, all of which interconvert. For simplicity, Formula VII(a) has been used exclusively throughout the specification and claims. However, it should be understood that Formula VII is nothing more than a shorthand notation for Formulae VII(a)–VII(d). It likewise goes without saying that Formulae XI, XIII and XVIII embrace the corresponding tautomeric forms, i.e, the formulae wherein the protons and | bonds are as in Formulae VII(b)–-VII(d).

The following examples show representative compounds encompassed by this invention and their synthesis. However, it should be understood that they are for purposes of illustration only.

EXAMPLE 1

2-t-Butyl-5-methylisoxazolium perchlorate

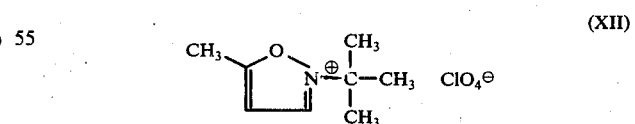

1 kg. of 5-methylisoxazole and 892 g. of t-butanol were stirred under nitrogen at 0° C. and 6.37 kg. of 60% perchloric acid were slowly added over a 2 ½ hour period with vigorous stirring at 0°–5° C. The resulting suspension was allowed to warm to room temperature and stirred overnight. The reaction mixture was then slowly added to a mixture of 20 l. of tetrahydrofuran and 10 l. of ether at 0°–10° C. over a 2 hr. period with stirring. The mixture was then cooled to −5° C. and stirred for an additional 2 hrs. The product (1.821 kg.) was washed well with ether, m.p. 120°-122° C. A second crop (171 g.) was obtained from the mother liquor, m.p. 118°-121° C.

EXAMPLE 2

N'-t-Butyl-3-hydroxybutenamidine

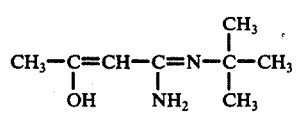
(XIII)

a. A solution of 100 g. 2-t-butyl-5-methylisoxazolium perchlorate in 200 ml. of methylene chloride was added with stirring to a mixture of 60 ml. of anhydrous amonia and 240 ml. of methylene chloride at −50° C. under nitrogen. The reaction mixture was allowed to come to room temperature and extracted with a saturated salt solution. The methylene chloride phase was dried over anhydrous magnesium sulfate. Removal of the methylene chloride at reduced pressure gave a solid. Recrystallization from ethyl acetate yielded the product, m.p. 118°-120° C. Further recrystallization from ethyl acetate raised the melting point to 126°-129° C.

b. A solution of 900 g. of 2-t-butyl-5-methylisoxazolium perchlorate in 1.80 l. of methylene chloride dried over aluminum oxide was added with stirring to a mixture of 900 ml. of freshly distilled ammonia and 900 ml. of methylene chloride dried over aluminum oxide at −50°-−60° C. with stirring. The reaction mixture was allowed to come to room temperature and was stirred overnight, and the trapped excess ammonia was stripped off at aspirator pressure at 20°-25° C. for 1 hr. The precipitated solids were removed by filtration and washed with methylene chloride. The combined filtrate and washings were washed twice with 2 l. portions of saturated potassium carbonate solution, dried well over anhydrous sodium sulfate and filtered. Removal of the methylene chloride at reduced pressure and a temperature of about 45° C. gave a solid. Crystallization from ethyl acetate and washing with ethyl acetate/ether gave a product (437 g.), m.p. 126°-129° C. A second crop (59 g.) was also obtained, m.p. 119°-125° C.

EXAMPLE 3

4-t-Butylamino-3-buten-2-one

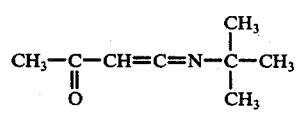
(XIV)

To a mixture of 700 ml. of triethylamine and 1.50 l. of methylene chloride dried over aluminum oxide cooled to −10°-−5° C., 1.0 kg. of 2-t-butyl-5-methylisoxazolium perchlorate was added portionwise over a 2 ½ hr. period, so as to maintain the temperature of the reaction mixture at −5°-−0° C., with vigorous stirring. Upon completion of the addition, the reaction mixture was stirred for an additional 1 hr. at −5°-−0° C. The reaction mixture was then poured over 38 l. of carbon tetrachloride at room temperature with vigorous stirring; oily solids separated. 15 lbs. of anhydrous sodium sulfate were added and the reaction mixture was stirred for 30 minutes. The suspension was filtered and the solids were washed with carbon tetrachloride. The combined filtrate-washings were concentrated at about 50° C. and reduced pressure to obtain a dark orange-yellow oil. Distillation at high vacuum yielded the product (522 g.), b.p. 54°-55° C. (0.8 mm Hg.).

EXAMPLE 4

3-Acetyl-2,6-di-t-butylamino-4-methylpyridine

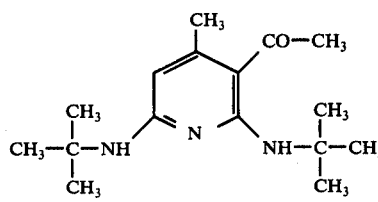
(V)

a. 3.17 g. (20.3 mmol.) of the amidine of Formula XIII (the product of Example 2) were suspended in 20 ml. of tetrahydrofuran and 12.7 ml. of a 1.6 M. solution of n-butyl lithium in hexane were added under nitrogen. The resulting exothermic reaction yielded a solution having a temperature of about 40° C. This solution was stirred at 30°-40° C. for 45 minutes and a solution of 2.80 g. (20.3 mmol.) of Compound XIV (Woodward et al., J. Amer. Chem. Soc. 88, 3169-3170 (1966).) in 8 ml. of tetrahydrofuran was added at 30°-38° C. followed by an additional 2 ml. of tetrahydrofuran. After 10 minutes a precipiate began to form. Stirring was contained for an additional 35 minutes and the reaction mixture was allowed to stand overnight. (Thin layer chromatographs of the reaction mixture after 45 minutes and the following morning were the same). The reaction mixture was cooled to −5° C. and 2 ml. of saturated ammonium chloride solution were added. Sufficient chloroform and a trace of methanol were added to form a solution which was evaporated at reduced pressure to obtain a mixture of oil and solids. This mixture was distributed between chloroform and water and a small amount (about ½ g.) of a white insoluble material was filtered off. The aqueous phase was re-extracted with chloroform and the chloroform phase was combined with the chloroform phase of the initial distribution. The combined chloroform phases were dried over anhydrous magnesium sulfate, filtered and evaporated to a brown oil (about 5 ½ g.). The brown oil was dissolved in a small volume of methanol at 40° C. and water was added until the resulting cloudiness persisted. The desired product crystallized out in the form of yellow needles which were washed with a small amount of a 1:1 mixture of methanol and water, m.p. 127°-128° C. Yield: 1.791 g.

N.M.R. (CDCl$_3$):
 1.43 δ (9 proton singlet)
 1.47 δ (9 proton singlet)
 2.32 δ (3 proton singlet)
 2.43 δ (3 proton singlet)
 4.60 δ (1 proton broad band, exchangeable)
 5.47 δ (1 proton broad singlet)
 9.94 δ (1 proton broad band, exchangeable)

I.R. (CHCl$_3$):
 3440, 2985, 1720 (v. weak), 1605-1580, 1525, 1450, 1420, 1390, 1360, 1290, 1210, 960 cm$^{-1}$ U.V. (CH$_3$OH):
 $\lambda_{max}$ 222 mμ ($\epsilon$ = 13,650)
 $\lambda_{max}$ 267 mμ ($\epsilon$ = 15,000)
 $\lambda_{max}$ 286 mμ ($\epsilon$ = 10,670)

λ$_{max}$ 368 mμ (ε = 20,500)
ED$_{50}$ (Test (a)): 2mg./kg. body weight
Test (b): 22% inhibition at 200 mg./kg. body weight.

b. A mixture of 468 g. of the amidine of Formula XIII and 6.0 l. of anhydrous tetrahydrofuran was stirred under nitrogen at room temperature and 1.92 l. of a 1.6 M. solution of n-butyl lithium in hexane were added dropwise at a rate such that the reaction mixture was maintained at a temperature of 20°–40° C. Upon completion of the addition, the reaction mixture was stirred at room temperature for an additional hour. A solution of 417 g. of the ketoketenimine of Formula XIV in 2 l. of anhydrous tetrahydrofuran was added dropwise with cooling so as to maintain the reaction temperature at 20°–25° C. Upon completion of the addition, the reaction mixture was stirred overnight at room temperature and then quenched with about 1.2 l. of saturated ammonium chloride solution, whereupon a thick white precipitate formed. 12 l. of methanol and 12 kg. of anhydrous sodium sulfate were added and the reaction mixture was filtered through diatomaceous earth. The filtrate was stripped to dryness at reduced pressure and the residue was dissolved in 25 l. of chloroform. The chloroform solution was extracted twice with 25 l. portions of water and once with 25 l. of saturated sodium chloride solution, dried over anhydrous sodium sulfate and filtered through silica gel. The clear yellow filtrate was stripped to near dryness at about 50° C. and reduced pressure and 5 l. of petroleum ether were added with cooling to obtain the product (553 g.), m.p. 127°–129° C.

EXAMPLE 5

3-Acetyl-2,6-di-t-butylamino-4-methylpyridine

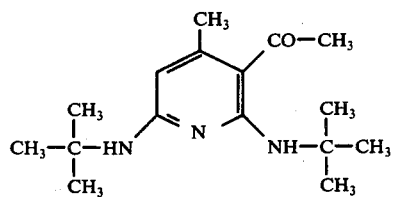
(V)

About 60 ml. of anhydrous ammonia were condensed into a flask containing 60 ml. of methylene chloride. The reaction mixture was maintained at a temperature not in excess of −30° C. under nitrogen and a solution of 50 g. of 2-t-butyl-5-methylisoxazolium perchlorate in 100 ml. of methylene chloride was added rapidly. The reaction mixture was allowed to come to room temperature and stirred for 4 days at room temperature. The methylene chloride was then removed at reduced pressure to obtain a gummy solid which was triturated with water to obtain a yellow solid. Recrystallization of the yellow solid from methanol/water yielded the product, m.p. 128°–129° C. Its spectra were identical with those of the product of Example 4(a).

EXAMPLE 6

Compound VIII 73.6 ml. of a 1.622 M. solution of n-butyl lithium in hexane (119 mmol.) were added to a solution of 18.6 g. (119 mmol.) of the amidine of Formula XIII in tetrahydrofuran at 25°–40° C. under nitrogen. Following the initial exothermic reaction, the reaction mixture was allowed to cool to about room temperature by stirring for one hour. A solution of 16.6 g. (119 mmol) of the ketoketenimine of Formula XIV in tetrahydrofuran was added dropwise at about room temperature (23°–25° C.). The reaction mixture was stirred overnight. Then, 4 ml. of a saturated ammonium chloride solution were added followed by sufficient methanol to form a darkly colored solution which was evaporated at reduced pressure. The residue was distributed between chloroform and water and the insoluble white solid was removed by filtration, m.p. 130° C. (decomp.) Yield: 23.2 g.

Elemental Analysis:
C, 55.8–56.0%
H, 8.2–8.4%
N, 11.7%

N.M.R. (Cd$_3$OD):
1.43 δ (singlet)
1.47 δ (singlet)
2.23 δ (singlet)
4.80 δ (singlet)

I.R. (nujol):
3370, 3280, 3120, 2880–2890, 1605, 1580, 1500, 1460, 1420, 1400, 1385, 1370, 1255, 1240, 1230, 1180, 1125, 1095, 1050, 1010, 990, 970 cm$^{-1}$ U.V. (methanol):
218 mμ (ε = 443 1% Solution)
264 mμ (ε = 638 1% Solution)
365 mμ (ε = 650 1% Solution)

The chloroform phase from the chloroform/water distribution was dried and evaporated at reduced pressure to a brown solid. Treatment of the brown solid with methylene chloride resulted in more insoluble white solid, m.p. 130° C. (decomp.).

EXAMPLE 7

3-Acetyl-2,6-di-t-butylamino-4-methylpyridine

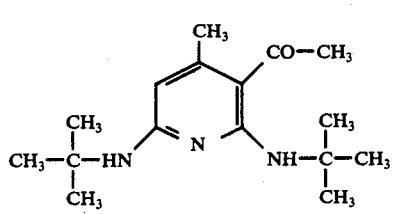
(V)

a. A small amount of Compound VIII (product of Example 6) was recrystallized from methanol/water resulting in a yellow, chloroform-soluble precipitate, m.p. 127°–128° C. (mixed melting point with authentic sample of Compound V was undepressed). Yield: 0.7 g.

b. The bulk of the product of Example 6 was boiled in aqueous methanol for 5 minutes. The yellow crystals which separated were filtered and washed with a 1:1 mixture of methanol and water to obtain the product, m.p. 127°–128° C. Yield: 16.56 g.

EXAMPLE 8

3-Acetyl-2,6-di-t-butylamino-4-methylpyridine.hydrobromide

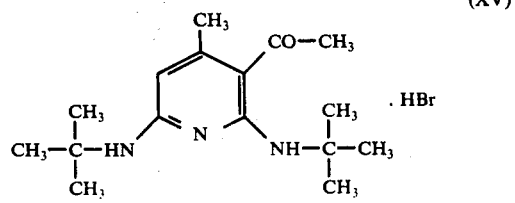
(XV)

The product was obtained by addition of a 1.6 N. solution of gaseous hydrogen bromide in ether dropwise to a solution of Compound V in ether at 0°-10° C. followed by stirring for 1 hr. The precipitate that formed was washed with ether and extracted with chloroform; activated charcoal was added, and the solution was filtered through diatomaceous earth and evaporated at reduced pressure. The product was crystallized from ether, m.p. 172°-175° C.

EXAMPLE 9

3-Acetyl-2,6-di-t-butylamino-4-methylpyridine.hydrochloride

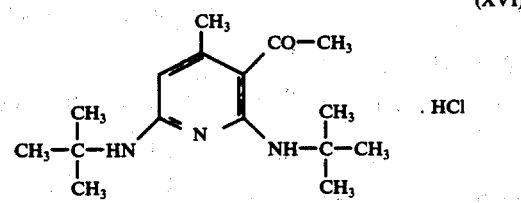

(XVI)

The product was obtained following the process of Example 8 using a 5.5 N. solution of gaseous hydrogen chloride in ether, m.p. 164°-166° C.

EXAMPLE 10

3-Acetyl-2,6-di-t-butylamino-4-methylpyridine.methanesulfonate

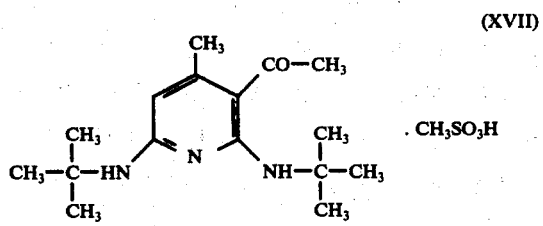

(XVII)

The product was obtained following the process of Example 8 using a solution of methanesulfonic acid in ether, m.p. 118°-121° C.

EXAMPLE 11

N'-t-butyl-3-hydroxy-3-(4'-methoxyphenyl)propenamidine

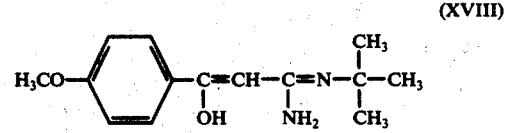

(XVIII)

Following the process of Example 2(a) or (b), the product was obtained from 2-t-butyl-5-(4'-methoxyphenyl)-isoxazolium perchlorate and ammonia, m.p. 166°-168° C.

EXAMPLE 12

2,6-di-t-butylamino-3-(4'-methoxybenzoyl)-4-methylpyridine (XIX)

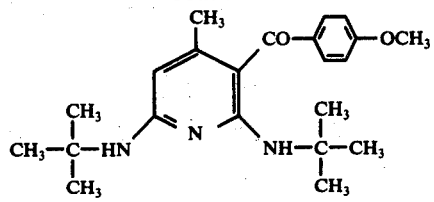

1.24 ml. of a 1.6 M. solution of n-butyl lithium in hexane were slowly added to a solution of 500 mg. of the amidine of Formula XVIII in 10 ml. of dry tetrahydrofuran stirred under nitrogen. The temperature of the reaction mixture rose to 35° C. during the addition. The reaction mixture was stirred for 15 minutes and 2.2 ml. of a 1 M. solution of the ketoketenimine of Formula XIV in dioxane were slowly added. The reaction mixture was then stirred for an additional 1 hr. and 1 ml. of saturated ammonium chloride solution was added. The reaction mixture was extracted with chloroform and water and the chloroform extract was dried over anhydrous sodium sulfate and evaporated down to an oil at reduced pressure. The oil was dissolved in ether and the ethereal solution was extracted with 2N. hydrochloric acid, washed twice with water, dried over anhydrous sodium sulfate and evaporated down at reduced pressure. The residue was crystallized from ether/heptane (280 mg.). Recrystallization gave the product (150 mg.), m.p. 127°-129° C.

EXAMPLE 13

2,6-di-t-Butylamino-3-cyano-4-methylpyridine

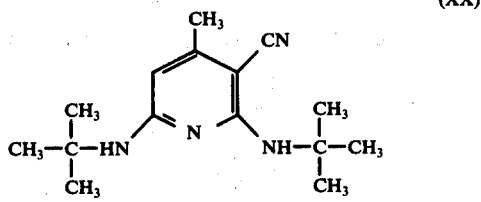

(XX)

1 g. (5.35 mmol.) of 2,6-dichloro-3-cyano-4-methylpyridine and approximately 40 ml. of t-butylamine (distilled from sodium hydride) were heated together in a reaction bomb at 200° C. for 5 hrs. Heating for an additional 4 hrs. at the same temperature produced no further change in the reaction mixture. The reaction mixture was allowed to stand overnight and was evaporated at reduced pressure to obtain a gummy solid. The gummy solid was partitioned between water containing a trace of sodium carbonate and chloroform, and the aqueous phase was re-extracted twice with chloroform. The three chloroform phases were combined, dried over anhydrous sodium sulfate and evaporated at reduced pressure. The residue was dissolved in 10 ml. of chloroform and diluted to 70 ml. with hexane. The small amount of crystals that formed were removed by filtration and the filtrate was applied to a column of 50 ml. of silica gel packed in 20% chloroform in hexane and eluted with the same solvent mixture. The first 130 ml. of eluate contained nothing, and the next 100 ml. of eluate were evaporated to obtain 6-t-butylamino-2-chloro-3-cyano-4-methylpyridine (0.49 g.), m.p. 109° C. The next fractions, containing the desired product, were combined and evaporated at reduced pressure and hexane was added. After evaporation of the hexane at reduced pressure, the residue was allowed to crystallize in the freezer to obtain the desired product (0.362 g.), m.p. 134°–138° C.

EXAMPLE 14

3-Acetyl-5-bromo-2,6-di-t-butylamino-4-methylpyridine

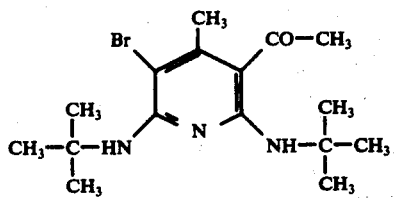

(XXI)

534 mg. (3 mmol.) of N-bromosuccinimide (recrystallized from water) were added in small portions to a solution of 831 mg. (3 mmol.) of 3-acetyl-2,6-di-t-butylamino-4-methylpyridine (Compound V) in 20 ml. of carbon tetrachloride and 5 ml. of ethanol, and the reaction mixture was allowed to stand overnight at room temperature. The reaction mixture was evaporated down at reduced pressure, and the residue was partitioned between ether and water. The organic phase was dried over anhydrous sodium sulfate and evaporated at reduced pressure to obtain yellow crystals. Recrystallization from methanol/water gave the product (990 mg.), m.p. 99°–100° C.

EXAMPLE 15

2,6-di-t-Butylamino-4-methylpyridine.methanesulfonate

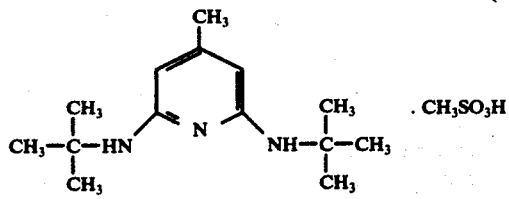

(XXII)

A mixture of 4.22 g. (15.2 mmol.) of 3-acetyl-2,6-di-t-butylamino-4-methylpyridine (Compound V), 1.00 ml. (15.4 mmol.) of methanesulfonic acid and 0.5 ml. (28 mmol.) of water in 50 ml. of methanol was refluxed for 3 hrs. The solids which separated upon cooling were removed by filtration and the filtrate was evaporated down. Trituration of the residue with ether gave a solid (4.0 g.), m.p. 168° C. (decomp.). Recrystallization from ethyl acetate gave the product (2.34 g.), m.p. 181°–182° C. A second crop (1.72 g.), m.p. 179°–181° C., was obtained from the mother liquor.

$ED_{50}$ (Test (a)): 12.3 mg./kg. body weight

EXAMPLE 16

2,6-di-t-Butylamino-4-methyl-3-propionylpyridine (IV)

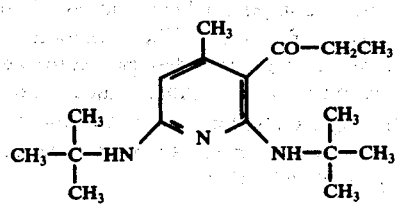

To a solution of 2.77 g. (10 mmol.) of 3-acetyl-2,6-di-t-butylamino-4-methylpyridine (Compound V) in about 30 ml. of dry tetrahydrofuran stirred under nitrogen at 0° C., 6.2 ml. of a 1.6M solution of n-butyl lithium in hexane (10.3 mmol.) was slowly added so as to maintain the temperature below 5° C. 0.8 ml. of methyl iodide was then added and the reaction mixture was allowed to come to room temperature over a 1 hr. period. (Thin layer chromatography (25% ethyl acetate/hexane) revealed a mixture of two products (approximately 50% and 25%) and starting material (approximately 25%)). The reaction mixture was partitioned between chloroform and water, the aqueous phase was re-extracted twice with chloroform and the combined chloroform phases were dried over anhydrous sodium sulfate and evaporated at reduced pressure. Since the desired product in pure form could not be obtained from the residue by crystallization, the residue was dissolved in a minimum amount of chloroform applied to 250 ml. of silica (2.5 cm. column diameter) and eluted with 50% toluene/hexane. The fractions containing the desired (major) product were combined and stripped to dryness at reduced pressure and the residue was recrystallized from methanol/water to obtain the product as yellow crystals (1.3 g.), m.p. 102°–103° C.

$ED_{50}$ (Test (a)): 3.1 mg/kg. body weight

The compound of this example may be converted into its pharmaceutically acceptable acid addition salts by conventional means and may be utilized for the treatment of diabetes and, particularly, obesity by administration to a host in need of such treatment.

EXAMPLES 17–28

Other compounds of Formula I that are synthesized by the processes of the foregoing examples are:

Example 17:
2,6-di-isopropylamino-4-ethyl-3-propionylpyridine

Example 18:
3-acetyl-5-chloro-2,6-di-t-butylamino-4-methylpyridine

Example 19:
3-acetyl-2,6-di-t-amylamino-4-methylpyridine

Example 20:
3-benzoyl-2,6-di-t-butylamino-4-methylpyridine

Example 21:
2,6-di-t-butylamino-3-(4'-methylbenzoyl)-4-methylpyridine

Example 22:
2,6-di-sec-butylamino-4-methylpyridine

Example 23:
2-t-amylamino-6-t-butylamino-4-methylpyridine

Example 24:
2,6-di-t-butylamino-3-methoxycarbonyl-4-methylpyridine

Example 25:
2,6-di-t-butylamino-3-carbamoyl-4-methylpyridine

Example 26:
2,6-di-t-butylamino-4-ethyl-3-propionylpyridine

Example 27:
3-cyano-2,6-di-isopropylamino-4-methylpyridine, m.p. 89°–90° C.

Example 28:
3-acetyl-2,6-di-(1,1-diethylpropylamino)-4-methylpyridine

The compound of each example may be converted by conventional means into its pharmaceutically acceptable acid addition salts.

The N.M.R. spectra were taken at ambient temperature on a 60 Mhz N.M.R. spectrometer and the chemical shifts are given in p.p.m. (δ) relative to tetramethylsilane. For anything other than a singlet, the indicated value is the midpoint of the peak.

What is claimed is:
1. A compound having the formula

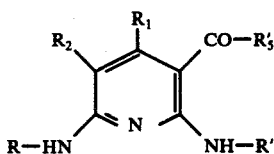

wherein
R is secondary alkyl of 3 to 7 carbon atoms or tertiary alkyl of 4 to 7 carbon atoms,
R' is secondary alkyl of 3 to 7 carbon atoms or tertiary alkyl of 4 to 7 carbon atoms,
$R_1$ is alkyl of 1 to 4 carbon atoms,
$R_2$ is hydrogen, chloro or bromo, and
$R_5'$ is alkyl of 1 to 4 carbon atoms,
or a pharmaceutically acceptable acid addition salt thereof.

2. A compound according to claim 1
wherein $R_2$ is hydrogen,
or a pharmaceutically acceptable acid addition salt thereof.

3. A compound according to claim 2
wherein
R is tertiary alkyl of 4 to 7 carbon atoms,
R' is tertiary alkyl of 4 to 7 carbon atoms,
$R_1$ is alkyl of 1 to 3 carbon atoms, and
$R_5'$ is alkyl of 1 to 3 carbon atoms,
or a pharmaceutically acceptable acid addition salt thereof.

4. A compound according to claim 1
wherein
R is tertiary alkyl of 4 to 7 carbon atoms, and
R' is tertiary alkyl of 4 to 7 carbon atoms,
or a pharmaceutically acceptable acid addition salt thereof.

5. A compound according to claim 4
wherein
$R_1$ is alkyl of 1 to 3 carbon atoms, and
$R_5'$ is alkyl of 1 to 3 carbon atoms,
or pharmaceutically acceptable acid addition salt thereof.

6. A compound according to claim 5
wherein
R is tertiary alkyl of 4 to 6 carbon atoms, and
R' is tertiary alkyl of 4 to 6 carbon atoms,
with the proviso that R and R' are identical,
or a pharmaceutically acceptable acid addition salt thereof.

7. A compound according to claim 6
wherein $R_2$ is hydrogen,
or a pharmaceutically acceptable acid addition salt thereof.

8. A compound according to claim 5
wherein
R is tertiary alkyl of 4 to 7 carbon atoms,
R' is tertiary alkyl of 4 to 7 carbon atoms,
$R_1$ is methyl or ethyl,
$R_2$ is hydrogen, chloro or bromo, and
$R_5'$ is methyl or ethyl,
or a pharmaceutically acceptable acid addition salt thereof.

9. A compound according to claim 8
wherein
R and R' are identical, and
$R_1$ and $R_5'$ are identical,
or a pharmaceutically acceptable acid addition salt thereof.

10. A compound according to claim 9
wherein
R is t-butyl,
R' is t-butyl, and
$R_2$ is hydrogen,
or a pharmaceutically acceptable acid addition salt thereof.

11. The compound according to claim 9 having the formula

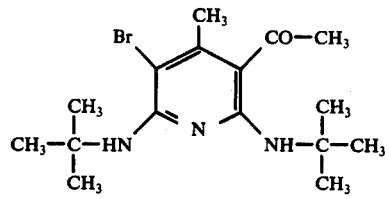

or a pharmaceutically acceptable acid addition salt thereof.

12. The compound according to claim 11 having the formula

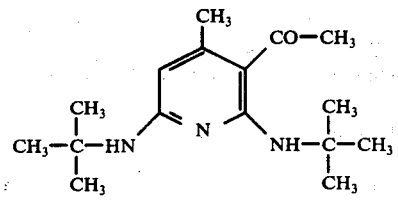

or a pharmaceutically acceptable acid addition salt thereof.

13. The compound according to claim 12 having the formula

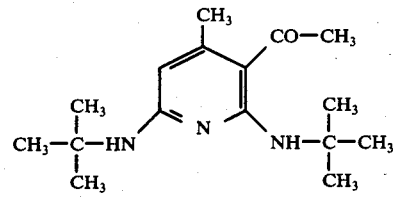

14. The compound according to claim 11 having the formula

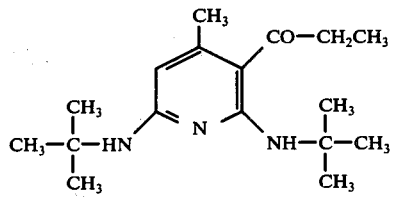

or a pharmaceutically acceptable acid addition salt thereof.

15. The compound according to claim 14 having the formula

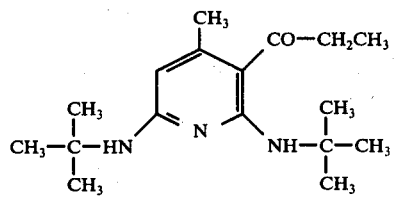

16. A pharmaceutical composition comprising a pharmaceutically effective amount of a compound of the formula

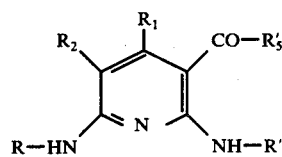

wherein
R is secondary alkyl of 3 to 7 carbon atoms or tertiary alkyl of 4 to 7 carbon atoms,
R' is secondary alkyl of 3 to 7 carbon atoms or tertiary alkyl of 4 to 7 carbon atoms,
$R_1$ is alkyl of 1 to 4 carbon atoms,
$R_2$ is hydrogen, chloro or bromo, and
$R_5'$ is alkyl of 1 to 4 carbon atoms,
or a pharmaceutically acceptable acid addition salt thereof, and a pharmaceutically acceptable carrier, said pharmaceutically effective amount being an amount effective for the treatment of obesity or diabetes.

17. A pharmaceutical composition according to claim 16, said composition being a solid or a sterile liquid.

18. A pharmaceutical composition according to claim 16 comprising a pharmaceutically effective amount of a compound of the formula

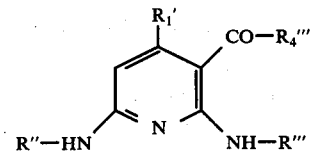

wherein
R" is tertiary alkyl of 4 to 7 carbon atoms,
R'" is tertiary alkyl of 4 to 7 carbon atoms
$R_1'$ is alkyl of 1 to 3 carbon atoms, and
$R_4'''$ is alkyl of 1 to 3 carbon atoms,
or a pharmaceutically acceptable acid addition salt thereof,
and a pharmaceutically acceptable carrier.

19. A pharmaceutical composition according to claim 18 comprising a pharmaceutically effective amount of the compound of the formula

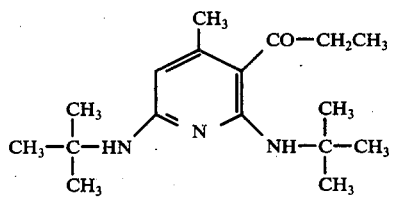

or a pharmaceutically acceptable acid addition salt thereof,
and a pharmaceutically acceptable carrier.

20. A pharmaceutical composition according to claim 19 comprising a pharmaceutically effective amount of the compound of the formula

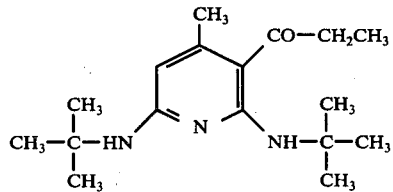

and a pharmaceutically acceptable carrier.

21. A pharmaceutical composition according to claim 20 in unit dosage form.

22. A pharmaceutical composition according to claim 18 comprising a pharmaceutically effective amount of the compound of the formula

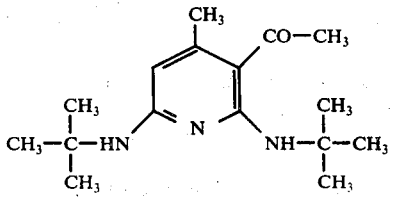

or a pharmaceutically acceptable acid addition salt thereof,
and a pharmaceutically acceptable carrier.

23. A method of treating obesity comprising administering to an obese host an effective amount of a composition according to claim 16, said effective amount being effective for the treatment of obesity.

24. A method of treating obesity according to claim 23 comprising administering to an obese host an effective amount of the compound of the formula

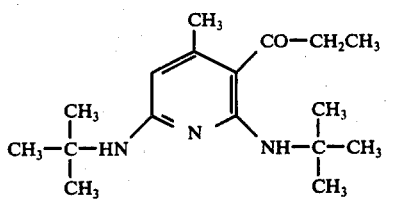

or a pharmaceutically acceptable acid addition salt thereof,
said effective amount being effective for the treatment of obesity.

25. A method of treating obesity according to claim 24 comprising administering to an obese host an effective amount of the compound of the formula

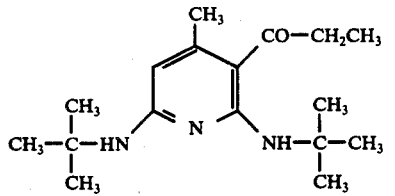

said effective amount being effective for the treatment of obesity.

26. A method of treating obesity according to claim 23 comprising administering to an obese host an effective amount of the compound of the formula

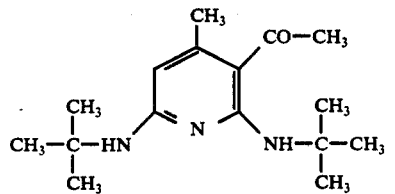

or a pharmaceutically acceptable acid addition salt thereof, said effective amount being effective for the treatment of obesity.

27. A method of treating diabetes comprising administering to a diabetic host an effective amount of a composition according to claim 16, said effective amount being effective for the treatment of diabetes.

28. A method of treating diabetes according to claim 27 comprising administering to a diabetic host an effective amount of the compound of the formula

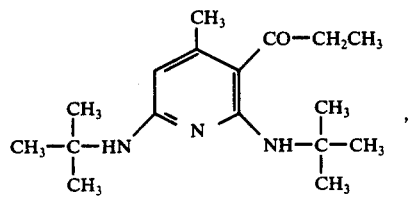

or a pharmaceutically acceptable acid addition salt thereof,
said effective amount being effective for the treatment of diabetes.

29. A method of treating diabetes according to claim 28 comprising administering to a diabetic host an effective amount of the compound of the formula

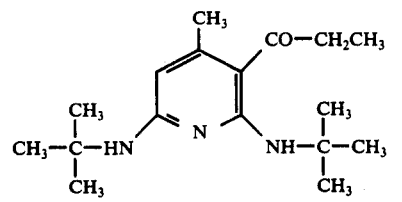

said effective amount being effective for the treatment of diabetes.

30. A method of treating diabetes according to claim 27 comprising administering to a diabetic host an effective amount of the compound of the formula

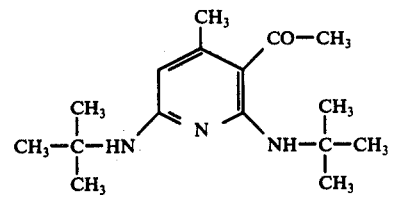

or a pharmaceutically acceptable acid addition salt thereof,
said effective amount being effective for the treatment of diabetes.

* * * * *